United States Patent [19]

Karnavas et al.

[11] Patent Number: 4,705,508
[45] Date of Patent: Nov. 10, 1987

[54] APPARATUS AND METHOD FOR RAPID INFUSION OF CIRCULATORY SUPPORTIVE FLUIDS

[75] Inventors: Alexander G. Karnavas, Forest Lake; Jorge A. Estrin, Mendota Heights, both of Minn.

[73] Assignee: Regents of the University of Minnesota, Minneapolis, Minn.

[21] Appl. No.: 781,774

[22] Filed: Sep. 30, 1985

[51] Int. Cl.$^4$ .............................................. A61M 1/36
[52] U.S. Cl. ...................................... 604/113; 604/4; 128/400
[58] Field of Search ................ 604/4, 80, 83, 113; 128/399, 400; 219/302

[56] References Cited

U.S. PATENT DOCUMENTS

| | | | |
|---|---|---|---|
| 2,102,523 | 12/1937 | Ferrara et al. | 219/302 |
| 3,552,393 | 1/1971 | Willgerodt . | |
| 3,614,385 | 10/1971 | Horstmann | 128/400 |
| 3,768,977 | 10/1973 | Brumfield et al. | 128/400 |
| 3,993,067 | 11/1976 | Schachet et al. . | |
| 4,014,328 | 3/1977 | Cluff et al. . | |
| 4,047,526 | 9/1977 | Reynolds et al. . | |
| 4,114,617 | 9/1978 | Turner et al. . | |
| 4,146,172 | 3/1979 | Cullis et al. . | |
| 4,177,816 | 12/1979 | Torgeson | 128/400 |
| 4,208,193 | 6/1980 | Munsch et al. . | |
| 4,243,531 | 1/1981 | Crockett et al. . | |
| 4,257,416 | 3/1981 | Prager . | |
| 4,295,495 | 10/1981 | Rosemeier et al. . | |
| 4,376,095 | 3/1983 | Hasegawa . | |
| 4,430,078 | 2/1984 | Sprague . | |
| 4,440,722 | 4/1984 | Luppi . | |
| 4,440,723 | 4/1984 | Gordon . | |
| 4,447,236 | 5/1984 | Quinn . | |
| 4,451,562 | 5/1984 | Elgas et al. . | |
| 4,540,399 | 9/1985 | Litzie et al. | 604/4 |

OTHER PUBLICATIONS

"Rapid Infusion Device May Untangle Trauma Care", *Wellcome Trends in Anesthesiology*, 8/85.
"Massive Transfusion".
"Pediatric Transfusion Problems".
"Complications of Blood Transfusion".
Brochure about Haemonetics Rapid Infusion System.

*Primary Examiner*—C. Fred Rosenbaum
*Assistant Examiner*—John D. Ferros
*Attorney, Agent, or Firm*—Merchant, Gould, Smith, Edell, Welter and Schmidt

[57] ABSTRACT

An apparatus and method for the rapid infusion of circulatory supportive fluid or blood is disclosed. The apparatus includes an enclosed housing for retaining the fluid prior to infusion, means for warming the fluid, means for circulating the fluid within the housing, means for inhibiting cellular damage of the fluid, means for permitting oxygenation of the fluid, and means for transfusing the fluid to the patient. The method includes the steps of providing an apparatus as described above, supplying it with circulatory supportive fluid or blood, warming the blood, and infusing it into a patient's vein at a rate of up to 3,000 or more ml. per minute.

The invention permits exceedingly rapid blood infusion at a single site, utilizing an apparatus which is easy to set up and very simple to use.

21 Claims, 2 Drawing Figures

APPARATUS AND METHOD FOR RAPID INFUSION OF CIRCULATORY SUPPORTIVE FLUIDS

TECHNICAL FIELD

This invention relates to an apparatus and method for the rapid infusion of circulatory supportive fluids such as blood into a patient. The apparatus includes an enclosed housing for retaining blood prior to infusion, means for warming blood within the housing, means for circulating the blood within the housing prior to infusion, means for inhibiting cellular damage to the blood during the circulation, means for permitting oxygen saturation of the blood, and means for transfusing the blood from the housing to a patient. Blood can be transmitted from the apparatus to the internal jugular vein of the patient, and can be infused at a rate of up to a physiological maximum rate.

BACKGROUND OF THE INVENTION

During surgery or in the emergency room, it is often necessary to infuse blood rapidly where massive blood loss or exsanguination has occurred. Patients having inadequate blood volume can suffer disastrous consequences.

Many situations give rise to the loss of great amounts of blood in a short period of time. These situations include hemorrhagic trauma resulting from injury to the patient, and a variety of major vascular, orthopedic, thoracic, and abdominal surgeries such as cancer surgery and liver transplantation.

In the past, surgical teams have had difficulty rapidly replacing blood lost from a patient. In a commonly used method of rapid infusion, several infusion sites are utilized at one time. Infusion bags or bags of stored banked blood are connected to the sites by intravenous tubing. Often, four or more personnel are required to manage the various infusion sites, manually squeezing blood bags or operating direct pressure pumps to infuse blood through the sites. Where warmed blood is desired for infusion, heating coils are often provided surrounding the infusion bags, thus requiring more complex apparatus which is nevertheless inefficient for warming at rapid infusion rates; this also requires multiple personnel. These and other similar currently used methods of rapid infusion have many drawbacks. Often, for example, where stored banked blood is used directly from bags, the chemistry of the blood utilized for infusion is inappropriate for the necessary high infusion rates of 1-3 liters per minute or more, and can have serious, even lethal effects on the patient. Further, the presence of numerous personnel monitoring the infusion sites and manually squeezing blood bags or operating pumps can create a chaotic atmosphere and distract others in the performance of their duties.

Utilizing conventional infusion methods, blood is often lost faster than it can be given and the patient goes into shock. In other situations, blood is infused fast enough but it is cold, acidic, and chemically imbalanced, leading to hypothermia and possibly cardiovascular instability.

Conventional rapid infusion methods also provide significant potential for contamination. The presence of multiple personnel, the use of multiple sites, and the process of opening numerous blood bags and attaching them to lines greatly increases the risk of contamination. This is of particular concern for liver transplant patients and other critically ill patient where sterile conditions are of extreme importance.

Further, blood infused by conventional methods is occasionally inadequately filtered and warmed, which can lead to severe consequences. It can also lack cost effectiveness, in view of the large number of people required to carry out the infusion and the length of time the patients generally must remain in intensive care after surgery requiring rapid infusion.

Lastly, the morbidity and mortality rates encountered with conventional massive transfusion or infusion techniques and apparatus are unacceptably high, particularly in liver transplant or resection operations.

Accordingly, a need exists for a rapid blood infusion apparatus and method which can successfully infuse large quantities of warmed, processed blood in a short time, which can be conveniently operated by one individual, which eliminates the need for multiple infusion sites on the patient, and which is easy to set up, operate, and maintain.

BRIEF DESCRIPTION OF THE INVENTION

We have invented a rapid blood infusion apparatus and method which can be easily set up and conveniently operated by a single individual, and more importantly, which eliminates the need for multiple infusion sites and which quickly and safely delivers blood products to the patient. The apparatus and method can deliver blood up to a physiological maximum rate which can vary from patient to patient, the blood having the proper blood chemistry and temperature for the individual patient's needs. It can be very quickly set up and ready for use with trauma victims where timing is critical. It eliminates the need for multiple personnel, thereby simplifying rapid infusion and creating a more orderly environment in the operating or emergency room. It is simple for use with low birth weight pediatric patients, as well as adult patients.

A significant advantage of the invention is that it provides infusion rates which can match exsanguination rates of severe rapid blood loss. Through use of this apparatus and method, hemorrhagic shock can be avoided, and morbitity and mortality rates decreased. Use of the invention can also reduce the patient's stay in the intensive care unit, thus providing greater cost-effectiveness than conventional apparatuses and methods.

The invention also provides for simplified logistics of blood product processing and infusion, because of the invention's simplicity compared to conventional techniques.

The invention also serves to optimize sterile techniques through the design of the apparatus and the simplified infusion procedure. Sterile technique is of great importance because infection is currently a leading cause of surgical fatality.

As a further advantage, the apparatus is compatible with other existing equipment, such as the Haemonetics Cell Saver ® unit.

The invention can also help oxygen delivery in patients with gas exchange problems, and can help prevent respiratory failure. It also allows for a more effective and direct control of the patient's basic physiological functions (i.e., temperature, pH, cardiac output, blood volume, serum electrolytes, etc.).

The invention has made certain radical operations, such as liver transplants, more successful. Bleeding can be a serious problem during such operations. A patient can exsanguinate in a matter of minutes. Through use of the invention, the patient's blood volume can be maintained until the vessels can be clamped, avoiding shock, cardiac arrest, and the need for resusitation.

As used herein, "blood" refers to circulation or circulatory supportive fluids including, but not limited to, blood, plasma expanders, artificial blood products such as those comprising Teflon material where for religious or other reasons a patient cannot receive actual blood components, and the like. For most situations where this invention will be used, the circulation supportive fluids will be whole human blood or packed red blood cells resuspended in normal saline, fresh frozen plasma, or Plasmalyte.

The apparatus of the invention comprises an enclosed housing for retaining blood prior to infusion. The housing has a top surface, a bottom surface, and a wall joining the top surface and the bottom surface. The enclosed housing also has two areas designated generally as an upper zone and a lower zone.

Positioned within the housing in the lower zone, the apparatus includes means for warming blood prior to infusion.

The apparatus further includes means for circulating the blood within the housing prior to infusion. This circulating means is attached or connected to the housing.

In the upper zone of the housing is provided means for inhibiting cellular damage during circulation of the blood.

Located on the housing is a means for providing oxygen saturation of and $CO_2$ removal from the blood prior to infusion.

Lastly, the apparatus comprises means for transfusing the blood from the housing to a patient. This means is, of course, connected to the housing.

The invention further relates to a method of rapidly infusing circulation supportive fluid or blood into a patient. The method comprises providing an apparatus having an enclosed housing for retaining blood prior to infusion, means for warming blood prior to infusion, means for circulating the blood within the housing prior to infusion, means for inhibiting cellular damage during blood circulation, means for providing oxygen saturation of the blood, and means for transfusing the blood from the housing to a patient; supplying blood to the apparatus; circulating the blood within the apparatus while heating the blood to a temperature of about 36°–40°C.; and infusing the blood from the apparatus to a patient's vein at rates of up to a physiological maximum, typically, up to about 3,000 ml. per minute.

DETAILED DESCRIPTION OF THE INVENTION

Figure 1:
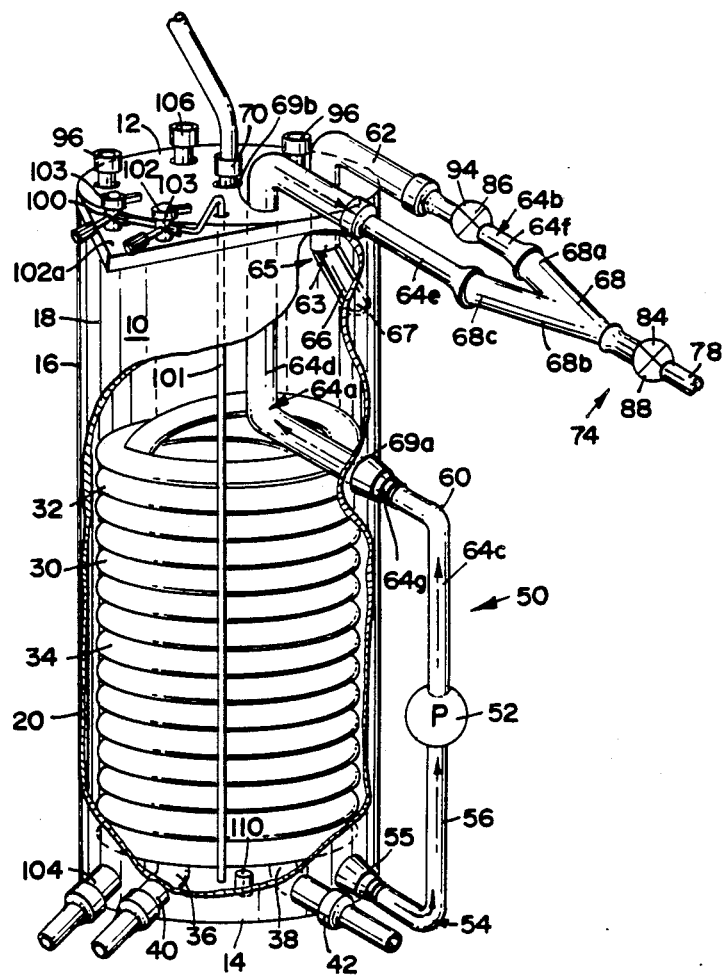
FIG. 1 is a perspective view generally viewed as from above and to the side of one embodiment of the rapid blood infusion apparatus incorporating the present invention.

Referring to the drawings, wherein like numerals represent like parts throughout the several views, there is generally designated at 5, a rapid blood or circulation supportive fluid infusion apparatus.

The apparatus 5 comprises enclosed housing or enclosure 10 having a top surface or wall 12, a bottom surface or wall 14, and a rigid side wall 16 connecting the top surface and the bottom surface. Typically, housing 10 will be generally cylindrical in shape. Top wall 12 and bottom wall 14 will generally be parallel, with rigid wall 16 being in the form of a curved surface extending perpendicularly between top 12 and bottom 14 to create an enclosed housing 10.

Housing 10 is designed for retaining blood prior to infusion to a patient. The housing will preferably hold about five liters of blood, in addition to certain features of the apparatus to be described hereinafter. A five liter housing is large enough to retain sufficient blood for many rapid infusion situations, and five liters is sufficient for replacement of the average adult's total blood volume. In addition, this size is small enough to permit mobility of the apparatus, and the cyclindrical shape makes it relatively easy to insert into a typical holder on an IV stand, which will be described hereinafter. Other sizes and shapes of housings can, of course, be used if desired.

The housing can be formed of any suitable blood compatible material. Preferably, the material will be a relatively hard or rigid transparent plastic. Polycarbonate materials are preferred because of their light weight, strength, and transparancy which permits viewing the blood level within the housing, and for ease and economy of manufacture. Other suitable plastics such as cellulose acetate butyrate or the like may also be used.

The housing includes an upper zone generally designated at 18, and a lower zone, generally designated at 20. Various components of the apparatus are located in either the upper or lower zones, as described hereinafter.

The apparatus 5 includes a means 30 for warming the blood within the housing. This warming means can be generally described as a heat exchanger, 32. Preferably, heat exchanger 32 comprises coiled tubing 34 set substantially within the lower zone 20 of housing 10. Tubing 34 is preferably formed of a single length of tubing, that is, one without joints or connections. Use of a single length helps prevent the possibility of water leaking into the blood; such leaks could be disastrous.

Tubing 34 has a first end 36 and a second end 38. Connected to first end 36 is an inlet port 40 in housing wall 16, located in lower zone 20 near bottom wall 14. Similarly, cooperatively connected to second end 38 is outlet port 42 in housing wall 16, located near bottom wall 14. Inlet and outlet ports 40 and 42 are designed for cooperative connection with a warm water supply. Typically they will be formed of rigid plastic or aluminum. The warm water enters or passes into coiled tubing 34 at first end 36 through inlet port 40, circulates through the coiled tubing and exits the tubing through second end 38 and outlet port 42.

Commercial units such as the Sarns heater cooler, Cardio-vascular Instruments, Inc., and Audronics, are available for supplying water to a heat exchanger. These units generally consist of a pump, hoses, and a thermostatically controlled heating element. They are typically powered by electricity. A preferred unit for use in this invention is the Audronics brand, because of its smaller size.

Placement of the inlet and outlet ports 40 and 42 is not critical, but their location at lower zone 20 near the bottom wall 14 of the housing tends to prevent interference of any hoses, pumps, and the like with the ease of operation of the apparatus.

It is preferred that coiled tubing 34 be formed of aluminum because aluminum is light weight, provides sufficient heat transfer, and is blood compatible. Other types of tubing may be used, for example, certain blood compatible rubber or plastic tubing, but such tubing generally provides significantly less heat exchange. Stainless steel tubing could also be used, but is significantly heavier and, therefore, contributes greatly to the weight of the apparatus, decreasing its ease of mobility.

Where coiled aluminum tubing is used, we suggest that the temperature of the water supplied to the tubing be about 42° C.

Too high a water temperature in tubing which provides good heat transfer may damage the blood. Generally, it is desirable that the heat exchanger be capable of warming five liters of blood within about 5–10 minutes, in the context of this invention.

Rapid blood infusion apparatus 10 further includes means 50 for circulating the blood within the housing prior to infusion. The blood is circulated to bring it to the proper temperature, to increase the oxygen content, if necessary, by way of a gas port to be described hereinafter, and to combine it with any required additives to alter the blood chemistry, or with medications required by the patient. In addition, once the blood has reached the proper temperature, level of oxygenation, etc., preferably circulation continues except during infusion itself until there is no more need for infusion. In this way, the apparatus and blood are maintained in a state ready for infusion.

Blood circulating means 50 comprises a pump 52, a blood outlet line 54, and a blood inlet line 60.

Pump 52 is located exterior to housing 10. Any suitable blood pump, such as a centrifugal, peristaltic, or roller pump can be utilized. Preferably, the pump will be calibrated to permit greater precision in its operation. Suitable pumps can be obtained from many medical suppliers, such as Sarns and Biomedicus. We recommend a pump having the ability to deliver a minimum of six liters per minute pumping action. The roller pump is preferred because of its mechanical simplicity, safety, relatively low cost, and portability. We currently prefer a Sarns 7000 modular pump available from Sarns, Inc.

Blood outlet line 54 is preferably located in the lower zone 20 of housing 10. Blood outlet line 54 includes port 55 extending through housing wall 16, and cooperatively connected thereto, suitable tubing segment 56 or other conduit extending from port 55 providing fluid communication between the interior of housing 10 and pump 52. Port 55 is preferably conventionally adapted for connection with tubing in various diameters. In particular, it is preferably adapted for connection with one-quarter inch by one-sixteenth inch and three-quarter inch by one-sixteenth inch tubing, in the nature of a reducer connector.

The conduit 56 can be any suitable material such as polyvinyl chloride (pvc) tubing, available commercially under many marks such as Tygon and Silastic. The currently preferred conduit is one-quarter inch by one-sixteenth inch pvc tubing, available from medical suppliers including Norton, the major supplier of Tygon tubing.

Blood inlet line 60 is located substantially at upper zone 18 of housing 10. It provides fluid communication between pump 52 and the interior of housing 10. Blood inlet line 60 can comprise port 62 extending into upper zone 18 of housing 10. Preferably, port 62 extends through top wall 12 of the housing, and includes a short tubular segment 63 extending, for example, about one to two inches into the interior of the housing, parallel to side wall 16. This extension 63 of port 62 serves to direct blood flow to a splash plate, hereinafter described in detail.

Blood inlet line 60 further comprises blood conduits 64a and 64b. The conduits together provide fluid communication between pump 52 and the interior of housing 10 by way of cooperative connection with a Y-connector 68 and through port 62.

Conduit 64a preferably comprises pvc tubing segment 64c leading from pump 52 to a rigid plastic tubular connector 64d. Connector 64d extends into sidewall 16 of housing 10 at point 69a and exits the housing at or near top wall 12, for example, at 69b. Cooperatively attached to connector 64d near top surface 12 of housing 10 is an additional conduit such as pvc tubing segment 64e, leading into Y-connector 68 (described hereinafter) at leg 68c.

Conduit 64b preferably comprises pvc tubing segment 64f leading from leg 68a of Y-connector 68 to port 62. Port 62 is preferably a rigid plastic tubular connector having extension 63. Tubing segment 64f is cooperatively connected to provide fluid communication between Y-connector 68 and port 62.

Y-connector 68 connects tubing segments 64e and 64f at a point outside housing 10. Y-connector 68 includes two outlet legs, or portals 68a and 68b, and one inlet leg or portal 68c. The term Y-connector as used herein refers to any connector having two outlet portals and one inlet portal, it being obvious that a T-connector would serve the same purpose.

As illustrated in the Figures, conduit 64a extends from pump 52 to portal 68c of Y-connector 68, while conduit 64b extends from portal 68a of Y-connector 68 and includes blood inlet port 62.

As illustrated, in the preferred embodiment conduit 64d enters housing 10 at an aperture 69a and exits housing 10 at an aperture 69b. This particular configuration aids in maintaining the warmth of the circulating blood. Apertures 69a and 69b are, of course, sealed securely around conduit 64d to prevent leakage or contamination. It is, of course, envisioned that several shorter conduits with conventional fittings at 69a and 69b may be utilized in place of single conduit 64d.

Tubing segment 64c is connected to end 64g of connector 64d. Like port 55, end 64g is preferably adapted for attachment to tubing of various diameters. Preferably, it is adapted in a conventional way for attachment to one-quarter and three-eights inch pvc tubing.

Blood circulating means 50 circulates blood retained in housing 10 from the interior of housing 10 through blood outlet line 54, through pump 52, and back into housing 10 through the blood inlet line 60. This permits the blood to be maintained at an even and constant temperature by way of heat exchanger 32, and also provides even distribution of any additives throughout the blood. It also prevents blood components from separating, and allows for faster infusion since the pump will already be operating and the blood already moving through the pump when infusion becomes necessary during surgery.

Circulating blood returning to housing 10 via blood inlet line 60 (through port 62) could be subject to cellular damage if the blood were to fall freely through upper zone 18 and contact with force the blood already within the housing. Cellular damage could also occur through the impact of blood falling onto the heat exchanger or other components within the housing. Therefore, means 65 is provided within the housing in upper zone 18 for inhibiting cellular damage during circulation of the blood.

Preferably, means 65 comprises a splash plate 66. Splash plate 66 directs the flow of blood from port 62 or extension 63 to wall 16 where it will gently flow down the wall to lower zone 20 of housing 10.

Splash plate 66 can be of any suitable size and shape to direct the blood flow from extension 63 to wall 16. In the preferred embodiment, splash plate 66 has a curved inner surface 67 or trough for directing the blood flow. The splash plate can be attached directly to extension 63, or at or near port 62 or extension 63 to collect the fluid flowing therefrom. It can be formed of any suitable blood compatible material. Plastic is preferred due to its light weight and low cost.

The rapid blood infusion apparatus 5 also comprises means for permitting or providing oxygen saturation of the blood. The providing means is typically at least one gas port 70. Generally, one gas port is sufficient. Gas port 70 is preferably located at top wall 12 of housing 10. The gas port permits oxygen saturation of and $CO_2$ diffusion from the blood prior to infusion. An oxygen line, for example, one-quarter inch rubber tubing connected to an oxygen source can be removably connected to gas port 70, and oxygen, under pressure, can in this way be introduced into the interior of housing 10. Oxygen will then diffuse into the blood while the blood is circulated in the housing prior to infusion.

Oxygen saturation of the blood is not always necessary, depending, for example, upon whether the blood has been processed, whether the patient's lungs are functioning well, and whether saline used to prime the apparatus has been supersaturated with oxygen gas.

Once the blood has become sufficiently saturated with oxygen (which can be determined by blood gas analysis), then the oxygen supply line can be removed and there is generally no further need for it during the course of an operation unless another supply of untreated blood is introduced into the apparatus.

The gas port 70 is preferably supplied with a conventional fitting or adaptor for connection to an oxygen line.

Figure 2:
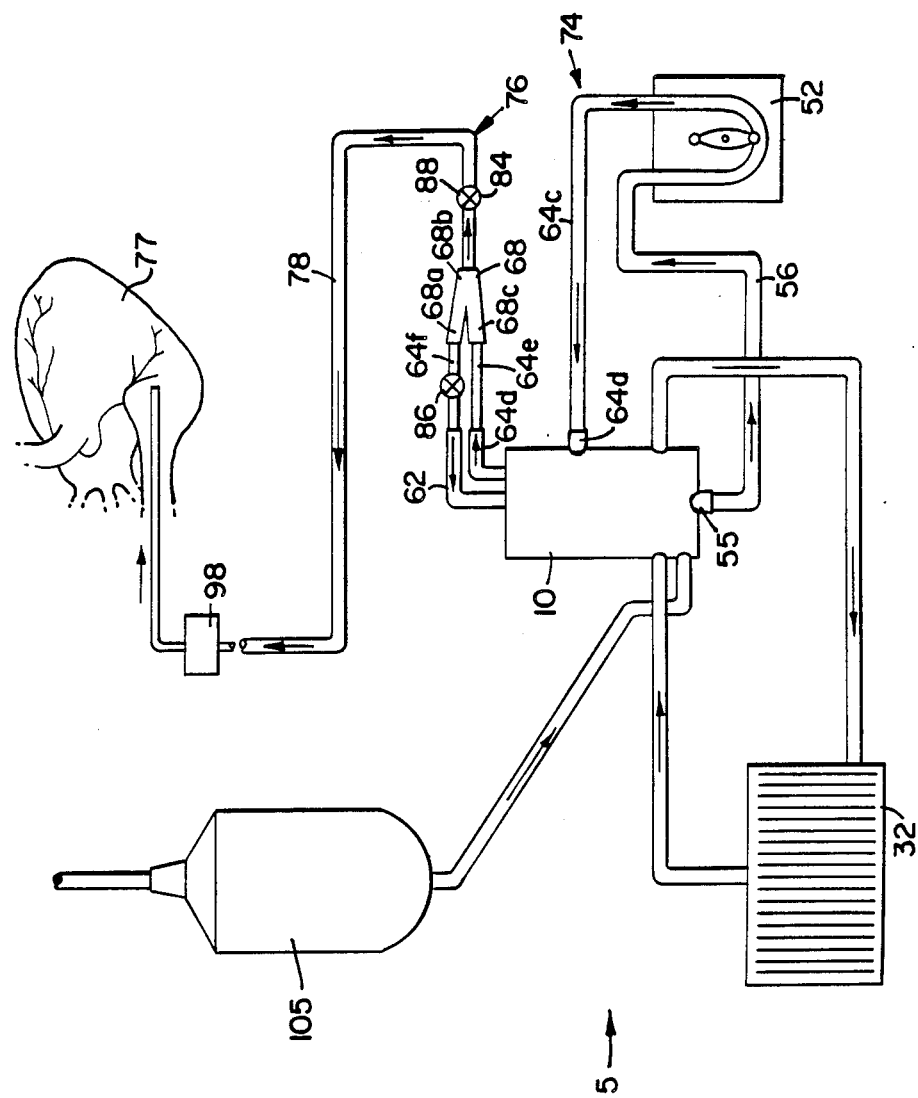
FIG. 2 is a schematic view of the apparatus and its use with a patient's circulatory system.

The apparatus further includes a means 74 for transfusing the blood from housing 10 to the patient. The transfusing means is cooperatively connected to the housing. It comprises blood outlet line 54, pump 52, and means 76 for providing fluid communication from the pump to the patient's circulatory system, which is represented in FIG. 2 at 77.

The providing means comprises conduit 64a providing fluid communication between pump 52 to inlet leg or portal 68c of Y-connector 68, and tubing segment or transfusion line 78 providing fluid communication between outlet leg or port 68b and the patient's circulatory system.

Transfusion line 78 can be any such line as is known in the art, for example, one-quarter inch pvc tubing. It is connected to an appropriate catheter which is inserted into a large venous vessel such as the internal jugular or femoral vein. If necessary, an artery may be used but it is less desirable because of increased risk of air embolization.

Preferably, for the most rapid infusion possible in the context of this invention, the catheter is inserted into the patient's internal jugular vein, and advanced into the right atrium of the heart. Other infusion sites may be used, but they typically will not provide the level of safety which can be achieved when the internal jugular is used.

The catheter can be any suitable catheter. For an adult, the 12, 14, 16 Bardic is generally preferred. For a child or larger infant, it is often preferable to utilize a Hickman catheter. For a very small infant, a 2.0 mm internal diameter Hickman catheter or an Angiopath ® No. 14 catheter can often be utilized successfully.

Mounted on the transfusion line is a first regulating means 84. The regulating means can open or close off the transfusion line. When infusion is desired, the transfusion line is opened. When infusion is no longer desired, or the rate of infusion is to be slowed, the regulating means can adjust or stop infusion of blood. The regulating means can be any suitable conventional clamp such as manually operated tubing clamp 88. Such a clamp provides for ease of operation.

Second regulating means 86 is connected to blood inlet line 60 at tubing segment 64f. This regulating means can be used to alter the blood flow back into the housing 10. It, too, is preferably a conventional manually operated tubing clamp such as tubing clamp 94.

To illustrate the use of clamps 88 and 94, prior to infusion the blood within housing 10 is circulated throughout the housing by way of circulating means 50, including pump 52. First tubing clamp 88 is set to close off transfusion line 78, while second tubing clamp 94 is set to allow blood flowage through blood inlet line 60. When infusion is desired, transfusion line 78 is opened to permit blood flow to the patient by adjusting tubing clamp 88, and second tubing clamp 94 is adjusted to reduce or eliminate recirculation of blood within the housing.

Rapid infusion apparatus 5 further comprises vent port 96 to permit the reduction of pressure within the housing. One or more vent ports may be utilized. In the preferred embodiment, two conventional vent ports are placed at opposite sides of top surface 12 of housing 10. Such ports provide constant pressure relief.

Apparatus 5 can further comprise one or more conventional blood filters 98 as a safety precaution. The blood filters can help eliminate the possibility of emboli, clots, air, and the like entering the patient's circulatory system with the infused fluid. Blood filter 98 can be any known type, such as a bubble trap, screen, or depth. The filter can be positioned any convenient place where tubing carries blood. Preferably, for increased safety it will be positioned near the end of transfusion line 78 where the blood enters the patient.

For increased safety, it is preferred that at least three blood filters be provided. They may be placed in any suitable locations. We suggest that a filter be used at the location where blood would enter cardiotomy 105 (described hereinafter), along tubing segment 64c, and along transfusion line 78 just before the blood enters the patient. Filters could also be placed at additional locations, for example, at quick prime port 106 (described hereinafter).

Other safety detectors and sensors known in the art can also be utilized to provide increased protection to the patient. For example, a pressure line (not shown) can be utilized to monitor the pressure of the blood flow entering the patient. Excessive pressure (which can arise, for example, if the catheter is improperly placed) can severely injure the patient. A purge line (not shown) or other safety valve can also be utilized to permit quick reduction of the pressure when necessary.

Rapid infusion apparatus 5 further includes one or more conventional blood sample ports. The blood sample ports permit the drawing of samples to test blood chemistry levels and obtain other information about the blood, and also provide a site for injecting medication or other additives to the blood, as needed. The preferred embodiment includes a first blood sample port 100 and a second blood sample port 102. They are mounted on housing 10 at upper zone 18, preferably on or near top wall 12 for ease of injection and blood drawing. As is conventional, they are each provided with a stopcock 103 to permit opening and closing of the port.

As shown in FIG. 1, and as in conventional, ports 100 and 102 may be mounted on a flange 102a or other edging piece attached at the top edge of housing 10 to facilitate accessability.

Both sample ports 100 and 102 are in fluid communication with a sample conduit 101. Sample conduit 101 comprises a narrow semi-rigid plastic tube or other suitable hollow shaft which extends into housing 10 to a location near bottom wall 14. Blood can be drawn from lower zone 20 of housing 10, through sample conduit 101 via either of sample ports 100 and 102. Alternatively, fluids such as medicaments can be injected into the blood within housing 10 by injecting them into sample port 100 or 102, from where they will travel into the blood supply via conduit 101.

The rapid infusion apparatus 5 further comprises at least one cardiotomy port 104. Cardiotomy port 104 permits the connection of housing 10 to a cardiotomy unit or blood reservoir 105, so that additional blood can be transferred to housing 10 with ease. Preferably, cardiotomy port 104 is located in lower zone 20 of housing 10 to inhibit cellular damage of blood entering the housing from cardiotomy unit 105. Cardiotomy unit 105 can be a simple blood reservoir to house extra blood.

Prior to placing blood in the cardiotomy, the blood may be processed, for example, in a unit such as the Cell Saver ®, an autologous blood recovery system by Haemonetics. This is particularly desirable for use with liver transplant or resection patients. If desired, other types of blood processing units such as a hemoconcentrator can be utilized.

The rapid infusion apparatus of this invention can further include a rapid or quick prime port 106, preferably mounted on top surface 12 of housing 10. Quick prime port 106 is adapted for connection to tubing which can be used to introduce fluids of various kinds into housing 10. For example, it is recommended to run saline solution through apparatus 5 to purge air from blood outlet line 54, pump 52, blood inlet line 60, transfusion line 78, etc., prior to initiating blood flow. The saline solution can be added to housing 10 through quick prime port 106. In addition, in some situations it is desirable to rapidly add quantities of blood to housing 10, for example, during infusion when more blood is required. While blood can be added through cardiotomy port 104 if another blood reservoir is ready, blood can also be quickly added from blood bags through quick prime port 106. If desired, a splash plate (not shown) could be located within housing 10 at the entrance of quick prime port 106.

In addition, rapid infusion apparatus 5 can comprise a temperature probe site 110 located on the housing. The temperature probe site, which can be designed in any suitable conventional fashion, permits monitoring of the blood temperature by use of a thermister probe. Suitable probes are available from suppliers such as Yellow Springs. The temperature probe site is preferably located at bottom wall 14 because the blood products collect at the bottom surface.

Preferably, apparatus 5 will include no defoaming components. Conventional defoamers, such as silicone impregnated sponges, can adversely affect the patient and are generally not needed in the context of this invention.

It is envisioned that apparatus 5 will be used with a suitable holder (not shown). The holder will permit its attachment to an IV pole, so that it can be easily transported and positioned where desired within the operating room. Such holders are conventional, and typically comprise a screw clamp for attachment to the desired position along the pole, and a support within which the device can removably rest. The IV pole typically includes wheels for easy transportation and maneuverability.

METHOD OF USE

The rapid blood infusion apparatus is easy to use. It can be set up within a matter of minutes. The preferred method of operating an apparatus having a five liter capacity is as follows.

First, with second tubing clamp 94 closed and first tubing clamp 88 open permitting circulation of blood within the rapid infusion apparatus, about one liter of 0.9 percent saline solution or other crystalloid solution such as Plasmalyte is added to housing 10 through quick prime port 106. Heat exchanger 32 is started. Pump 52 is started and the saline solution is caused to flow through the system to displace air. Then, second tubing clamp 94 is opened and first tubing clamp 88 is closed off, permitting the solution to pass through the transfusion line to flush air or other impurities from it. The transfusion line is then shut off by closing second tubing clamp 94 and opening first tubing clamp 88.

The crystalloid solution is removed from the apparatus, the pump is turned off, and five liters of blood or other circulatory supportive fluids are added to housing 10 through quick prime port 106 or cardiotomy port 104. The blood can comprise stored banked blood; filtered, washed, and packed red blood cells suspended in sterile normal saline; the patient's salvaged shed blood; or other blood products such as fresh frozen plasma.

Pump 52 is restarted to circulate the blood within apparatus 5. During circulation, if necessary, oxygen can be provided through gas port 70 until the blood reaches its oxygen saturation point or the desired level of oxygen saturation is achieved, at which time the oxygen source is removed. The gas port is left open to serve as an additional vent site.

With continued circulation, the chemistry and temperature of the blood is adjusted, as necessary, to achieve the desired levels for the particular patient and type of surgery. Some aspects of the blood chemistry will generally be adjusted, if necessary, before the blood is added to cardiotomy 105 or housing 10.

We have found that with this apparatus, excellent results can be seen in many patients if the blood chemistry and temperature is adjusted as necessary to achieve normal or nearly normal physiological values within the following ranges: hematocrit of about 25–45% (preferably 30±5%); potassium of about 3–6 mEq/L, and temperature of about 36°–40° C. (preferably 37±1° C.).

In addition, it can be desirable to achieve a pH of about 6.8–7.4 (preferably 7.2±0.2), a sodium level of about 140±10 mEq/L (preferably 140±5 mEq/L), and a bicarbonate level of 18±2 mEq/L.

It can also be desirable, for example, when a patient's lungs are functioning poorly, to achieve an oxygen saturation of 95-99%. The $pCO_2$ of the blood will preferably be about 35±5 torr.

It is not always necessary, but highly desirable, that the blood chemistry and temperature be within the ranges indicated above. This depends in large part on how well the patient's lungs, kidneys, liver, and other organs are functioning, the patient's general health, the patient's age, and the nature and urgency of the need for infusion.

In some instances, for example, where a car accident victim is likely to die without immediate infusion, it may be acceptable, for a short time, to infuse warm but otherwise unaltered stored banked blood until appropriate correction can be made. This blood may fall outside all of the ranges except the temperature range.

For most patients, as a minimum, the hematocit and potassium levels and the temperature should fall within the ranges described previously.

Many patients are able to accept blood with a pH outside the given range, but it is preferable to have the pH within the given range. This is of particular importance where the patients lacks the function of a major organ such as the heart, kidneys, or liver.

We have found that the above levels, taken together, are particularly desirable in treating liver transplant or resection patients, ranging in age from 6 months to 54 years.

The blood chemistry levels can be achieved in various ways known to one skilled in the art. Generally, the potassium level of stored banked blood will far exceed that which is safe at the rapid infusion rates of the invention. We have found it most advantageous in the context of this invention to lower the potassium level, when necessary, by blood cell washing prior to addition of the blood to apparatus 5.

The blood cell washing can be accomplished by mixing and thereby washing the cells with saline solution, then utilizing a high speed centrifuge to separate the cells from the saline solution. The washed cells are then resuspended in a plasma product such as fresh frozen plasma. The Cell Saver ® unit is currently preferred for the washing process.

The blood washing process also appears to reduce post-transfusion respiratory failure which is often seen after conventional blood infusion methods are used. We theorize that the removal of white blood cells in the washing process relates to the reduction of such difficulties.

The washing process also helps eliminate cell conglomerates which can form in stored, banked blood, reducing the risk of blood clots.

The pH, $pCO_2$, oxygen saturation level, hematocrit, and temperature can be adjusted while the blood is within housing 10. It is also possible to raise the potassium level, if desired, while the blood is within the housing. The sodium and bicarbonate levels can typically be raised (but not lowered) while the blood is within housing 10.

As the blood is being prepared, the catheter can be inserted into the desired site. We have found that in most instances, best results are achieved if the catheter is inserted into the right atrium of the heart through the patient's internal jugular vein. Generally a single site permits sufficiently rapid infusion within the context of this invention.

When infusion is required, the transfusion line is opened through use of the second tubing clamp 94, and blood inlet port 62 and tubing segment 64b can be shut off utilizing first tubing clamp 88.

With this invention, blood can be infused at a rate of up to about the physiological maximum for the individual patient. This maximum could be determined or would be known by one skilled in the art. It varies from patient to patient and depends largely on the patient's size. However, currently it would be difficult to obtain and suitably prepare sufficient blood for rates above 3,000 ml. per minute. It would also be difficult to keep apparatus 5 supplied with blood at these higher rates. Generally, in view of the difficulty in obtaining sufficient blood and keeping apparatus 5 supplied with prepared blood for rates higher than three liters per minute, the rate will be up to about three liters per minute. More typically, the rate will be from about 45 to 2,000 ml. per minute. The desired rate can be determined by appropriate hemodynamic measurements, e.g., cardiac output, main pulmonary artery pressures, right atrial pressure, and systemic blood pressure. Mechanically, the rate is adjusted by varying the rpm's of the pump.

When infusing processed blood, it is generally necessary to separately infuse cryoprecipitate and platelets to maintain the desired serum levels of fibrinogen platelets. Particularly for liver transplant or resection patients, we have found that their serum levels should be maintained at about 0.4 gram percent of fibrinogen and 250,000 platelets per ml. of blood. Other fluids or medications may also be indicated in particular situations.

Other modifications of the invention will be apparent to those skilled in the art in light of the foregoing description. Accordingly, the invention is not limited to the embodiments described herein, or to the use of elements having specific configurations and shapes as presented herein. All alternative modifications and variations of the present invention which follow in the spirit and scope of the appended claims are included.

We claim:

1. An apparatus for rapid infusion of circulatory supportive fluid into a patient, which comprises:
    (a) an enclosed housing for retaining a predetermined quantity of circulatory supportive fluid prior to infusion, said housing having a top surface, a bottom surface, and a surrounding side wall joining the top surface and the bottom surface, and having an upper zone and a lower zone therein;
    (b) positioned within the housing in the lower zone, heat exchanger means for warming the fluid prior to infusion;
    (c) attached to the housing, in fluid communication with the upper and lower zones therein, means including an exterior pump for circulating the fluid within the housing prior to infusion;
    (d) located on the housing, means for permitting oxygen saturation of the fluid within said housing prior to infusion; and
    (e) connected to the circulating means, means for selectively connecting the circulating fluid in fluid communication with the patient to effect rapid infusion.

2. The apparatus of claim 1, wherein the housing comprises a polycarbonate material, and has the capacity for holding up to about 5 liters of blood.

3. The apparatus of claim 1, wherein the heat exchanger comprises coiled aluminum tubing having a first end and a second end, and inlet port in the housing wall at the lower zone connected to the first end, and an outlet port in the housing wall at the lower zone connected to the second end, such that warm water can pass into the coiled aluminum tubing through the inlet port and out of the coiled aluminum tubing through the outlet port.

4. The apparatus of claim 1 wherein the means for permitting oxygen saturation comprises a gas port located at the upper zone of the housing.

5. The apparatus of claim 1 which further comprises at least one vent port located at the top surface of the housing to reduce pressure build-up within the housing.

6. The apparatus of claim 1 which further comprises a fluid sample port mounted on the housing in the upper zone for drawing samples of the fluid therein.

7. The apparatus of claim 1 which further comprises a cardiotomy port mounted on the housing in the lower zone for attachment to a blood reservoir for providing fluid to the apparatus.

8. The apparatus of claim 1 which further comprises a quick prime port mounted on the top surface of the housing for rapid addition of fluid into the housing.

9. The apparatus of claim 1 which further comprises a temperature probe site located on the housing to permit measurement of the fluid temperature.

10. An apparatus for rapid infusion of circulatory supportive fluid into a patient, which comprises:
(a) an enclosed housing for retaining a predetermined quantity of circulatory supportive fluid prior to infusion, said housing having a top surface, a bottom surface, and a surrounding side wall joining the top surface and the bottom surface, and having an upper zone and a lower zone therein;
(b) positioning within the housing in the lower zone, means for warming the fluid prior to infusion;
(c) attached to the housing, means for circulating the fluid within the housing prior to infusion;
(d) located on the housing, means for permitting oxygen saturation of the fluid prior to infusion; and
(e) connected to the circulating means, means for selectively connecting the circulating fluid in fluid communication with the patient to effect rapid infusion;
said fluid circulating means including a pump exterior to the housing, a fluid outlet line at the lower zone of the housing providing fluid communication between the interior of the housing and the pump, and a fluid inlet line at the upper zone of the housing providing fluid communication between the pump and the interior of the housing such that fluid is circulated from the interior of the housing through the fluid outlet line, through the pump, and back into the housing through the fluid inlet line.

11. The apparatus of claim 10 wherein the pump is a calibrated roller pump.

12. The apparatus of claim 10 wherein the means for selectively connecting the fluid with the patient comprises the fluid outlet line, the pump, and means for providing fluid communication from the pump to the patient's circulatory system.

13. The apparatus of claim 12 which further comprises a first means for regulating fluid flow back to the housing, and a second means for regulating fluid flow to the patient.

14. The apparatus of claim 13 wherein the first means for regulating fluid flow comprises a tubing clamp.

15. The apparatus of claim 13 wherein the second means for regulating fluid flow comprises a tubing clamp.

16. The apparatus of claim 13 which further comprises a blood filter connected between the patient and the apparatus.

17. An apparatus for rapid infusion of circulatory supportive fluid into a patient, which comprises:
an enclosed housing for retaining fluid prior to infusion, having a top surface, a bottom surface, and a wall joining the top surface and the bottom surface, and having an upper zone and a lower zone;
positioned within the housing in the lower zone, means for warming the fluid prior to infusion;
attached to the housing, means for circulating the fluid within the housing prior to infusion;
set within the housing in the upper zone, means for inhibiting cellular damage during circulation of the fluid;
located on the housing, means for permitting oxygen saturation of the fluid prior to infusion;
connected to the housing, means for transfusing the fluid from the housing to a patient;
said fluid circulating means including a pump exterior to the housing, a fluid outlet line at the lower zone of the housing providing fluid communication between the interior of the housing and the pump, and a fluid inlet line at the upper zone of the housing providing fluid communication between the pump and the interior of the housing such that fluid is circulated from the interior of the housing through the fluid outlet line, through the pump, and back into the housing through the fluid inlet line; and
said cellular damage inhibiting means including a splash plate mounted within the housing in the upper zone, cooperatively placed with respect to the fluid inlet line to reduce cellular damage of fluid entering the housing from the fluid inlet line.

18. Apparatus for rapid blood infusion, comprising:
an enclosed housing for retaining a predetermined quantity of blood prior to infusion, said housing having upper and lower zones;
heat exchanger means positioned in the lower zone of said housing for warming blood therein;
an external pump with an inlet connected in fluid communication with the lower zone of said housing, and an outlet connected in fluid communication with the upper zone of said housing, for continuously circulating the blood therein; and
means for selectively connecting the outlet of said pump in fluid communication with a patient for blood infusion at up to a physiological maximum rate.

19. The apparatus of claim 18, wherein said heat exchanger means comprises a coiled aluminum tubing having an inlet and an outlet connected through said housing.

20. The apparatus of claim 18, wherein said connection means comprises:
a connector having an inlet connected in fluid communication with the outlet of said pump, a first outlet connected in fluid communication with the upper zone of said housing, and a second outlet for connection in fluid communication with a vein in the patient;

a first normally opened clamp connected to the first outlet of said connector; and
a second normally closed clamp connected to the second outlet of said connector.

21. The apparatus of claim 18, further including:
a splash plate positioned in said housing in cooperative relationship with the outlet of said pump to inhibit cellular damage to the blood during circulation.

* * * * *